(12) United States Patent
Kolter et al.

(10) Patent No.: US 7,094,831 B2
(45) Date of Patent: Aug. 22, 2006

(54) AQUEOUS POLYMER DISPERSION

(75) Inventors: Karl Kolter, Limburgerhof (DE);
Maximilian Angel, Schifferstadt (DE);
Katrin Zeitz, Ludwigshafen (DE)

(73) Assignee: BASF Aktiengellsellschaft, Ludwigshafen (DE)

( * ) Notice: Subject to any disclaimer, the term of this patent is extended or adjusted under 35 U.S.C. 154(b) by 0 days.

(21) Appl. No.: 10/381,372

(22) PCT Filed: Sep. 25, 2001

(86) PCT No.: PCT/EP01/11053

§ 371 (c)(1),
(2), (4) Date: Mar. 25, 2003

(87) PCT Pub. No.: WO02/26845

PCT Pub. Date: Apr. 4, 2002

(65) Prior Publication Data

US 2003/0187122 A1 Oct. 2, 2003

(30) Foreign Application Priority Data

Sep. 29, 2000 (DE) ................................ 100 48 888
May 10, 2001 (DE) ................................ 101 22 786

(51) Int. Cl.
*C08L 29/00* (2006.01)
(52) U.S. Cl. ................ 524/800; 524/457; 524/458; 524/801; 524/802; 524/804; 524/832; 524/845
(58) Field of Classification Search ............... 524/800, 524/801, 802, 804, 832, 845, 457, 458
See application file for complete search history.

(56) References Cited

U.S. PATENT DOCUMENTS

| | | | | |
|---|---|---|---|---|
| 4,440,896 A | * | 4/1984 | Schuppiser et al. | 524/458 |
| 4,746,579 A | * | 5/1988 | Yannich et al. | 428/522 |
| 5,252,704 A | | 10/1993 | Bright et al. | |
| 6,001,916 A | * | 12/1999 | Walker et al. | 524/459 |
| 6,046,277 A | | 4/2000 | Kolter et al. | |
| 6,329,472 B1 | * | 12/2001 | Kim et al. | 525/326.9 |
| 6,552,115 B1 | * | 4/2003 | Zecha et al. | 524/457 |
| 6,716,941 B1 | * | 4/2004 | Kerr et al. | 526/202 |

FOREIGN PATENT DOCUMENTS

| | | |
|---|---|---|
| DE | 197 09532 | 9/1989 |
| DE | 43 41 156 | 2/1995 |
| FR | 977 296 | 3/1951 |

OTHER PUBLICATIONS

Fikentscher, Cellulosechemie, Bd.13, 58-64 (1932).
Fikentscher, Cellulosechimie, Bd. 13, 71-74 (1932).

* cited by examiner

*Primary Examiner*—David W. Wu
*Assistant Examiner*—Henry S. Hu
(74) *Attorney, Agent, or Firm*—Novak Druce & Quigg, LLP

(57) ABSTRACT

An aqueous polymer dispersion prepared by free-radical polymerization of vinyl acetate in the presence of at least one ionic emulsifier, at least one free-radical initiator and at least one protective colloid, wherein the polymerization is carried out in the presence of a polymerization regulator and wherein the ratio by weight of protective colloid to ionic emulsifier is at least 4:1 and wherein the ratio by weight of vinyl acetate monomer to protective colloid is between 19:1 and 4:1.

26 Claims, No Drawings

AQUEOUS POLYMER DISPERSION

The invention relates to an aqueous polymer dispersion prepared by free-radical polymerization of vinyl acetate, to a process for preparing an aqueous polymer dispersion of this type, and to the use thereof.

U.S. Pat. No. 5,252,704 discloses polymer powders which can be redispersed in water and which are prepared using polyvinylpyrrolidone (PVP) as dispersant. The polymer powders are prepared with use inter alia of vinyl esters in a conventional emulsion polymerization. PVP is added to the emulsion before the spray drying. The polymer powders are intended in particular as additives for cement mixtures.

DE 43 41 156 C1 discloses the use of plastic dispersion powders which are redispersible in water as pharmaceutical carriers in drug forms with controlled delivery of active ingredient, the powders having a core/shell structure with particular values of Tg for the core polymers and shell polymers.

DE 197 09 532 A describes the use of redispersible polymer powders or polymer granules for coating pharmaceutical or agrochemical dosage forms, the powders or granules consisting of 10 to 95% by weight of polyvinyl acetate and 5 to 90% by weight of an N-vinylpyrrolidone-containing polymer and, where appropriate, other additives.

For producing pharmaceutical dosage forms there are frequently used, as in DE 197 09 532, polymer powders which must be redispersed in water to produce these dosage forms. The reasons for this preparation of redispersible powders is that it is frequently impossible to stabilize the aqueous preparations appropriately for them to comply with the great demands made on starting materials for pharmaceuticals. Thus, for example, there must be no microbiological attack nor any increase in particle size, to say nothing of coagulation or sedimentation, because reliable production of the pharmaceutical is endangered thereby. The aqueous preparations are often stable only for some weeks. To prolong the stability, the aqueous preparations are converted into powders from which it is necessary in turn to prepare an aqueous preparation by stirring into water before use. This procedure consumes a large amount of energy and time and the thermal and mechanical stresses on the product during spray drying and stirring change the original properties. In addition, the reproducibility of important properties of the dosage forms, such as, for example, the release of active ingredient, is often poor because redispersible powders frequently result in coatings which adhere poorly, do not form complete films and are inhomogeneous. One reason for this is certainly that it is never possible to obtain a 100% redispersion of the powders, and such redispersions therefore always contain proportions of coarse particles or particle agglomerates (larger than 1 µm in diameter). A shift in the average particle diameter to values greater than 300 nm is enough to result in poor use properties.

Solid pharmaceutical dosage forms such as tablets, capsules, pellets, granules, crystals etc. are coated, i.e. provided with a film coating, for a wide variety of reasons. Thus, for example, it is possible to mask an unpleasant odor or taste and improve the swallowability. The stability of the active ingredient may be increased by the coating since less water vapor and oxygen reaches the interior of the tablets. The dosage forms have a better appearance and can be distinguished better by incorporating dyes. In addition, it is possible in particular to adjust the rate of release of active ingredient by the film coating. These criteria also apply in a similar way to agrochemical dosage forms.

In general, a distinction is made between instant release forms and sustained or slow release forms.

The intention with instant release forms is to release the active ingredient in the shortest possible time. In these cases the coating must impede release of the active ingredient from the core only slightly or not at all. In pharmaceutical technology, instant release forms are preparations from which more than 80% of the active ingredient are released within one hour.

By contrast, release from sustained release forms is delayed in order, for example, to avoid plasma level peaks and thus possible side effects, or to reduce the frequency of intake. In the so-called coated sustained release forms, a film coating slows down the release of the drug substance. Frequently employed for this purpose are water-insoluble cellulose derivatives such as ethylcellulose or (meth)acrylate copolymers, in particular Eudragit® NE, RS and RL (Röhm Pharma). For Eudragit® RS and RL it is recommended to add from 10 to 20% by weight, based on the film former, of plasticizer. An even higher plasticizer content (about 30% by weight) is indispensable for ethyl cellulose. Only Eudragit® NE requires no plasticizer because it has a very low glass transition temperature and minimum film-forming temperature. However, this causes it to be tacky and difficult to process.

It is an object of the present invention to provide starting materials for producing in particular pharmaceutical dosage forms, which are very stable on storage, which can be processed very easily, which in particular easily result in good, homogeneous film coatings with very reproducible release and which, where appropriate, need not be prepared from powders which are initially dried and then redispersed in $H_2O$.

We have found that this object is achieved by an aqueous polymer dispersion prepared by free-radical polymerization of vinyl acetate in the presence of at least one ionic emulsifier, at least one free-radical initiator and at least one protective colloid, wherein the polymerization is carried out in the presence of a polymerization regulator and wherein the ratio by weight of protective colloid to ionic emulsifier is at least 4:1, preferably at least 8:1, particularly preferably in the range between 8:1 and 12:1, and wherein the ratio by weight of vinyl acetate monomer to protective colloid is between 19:1 and 4:1, preferably between 15:1 and 6:1.

A preferred embodiment of the abovementioned aqueous polymer dispersion is prepared by free-radical polymerization at a pH in the range from 1 to 7, particularly preferably in the range from 3 to 6.

It has proved advantageous in this connection for the pH to be kept constant in the range from pH 1 to pH 7 during the polymerization by addition of a reagent with a basic action. A pH kept constant means, both during and after the polymerization, a pH with variations in the region of +/−1.5, preferably +/−1, particularly preferably +/−0.5 units.

The reagents with a basic action used for the purpose of the invention are preferably alkali metal or alkaline earth metal hydroxides, particularly preferably aqueous solutions of alkali metal hydroxide or an alkaline earth metal hydroxide - especially sodium hydroxide or potassium hydroxide solution - and aqueous ammonia solutions.

It has proved to be particularly advantageous for the pH to be kept constant during the polymerization by addition of a buffer system.

Buffer systems mean conventional buffer and/or polymeric buffers.

Examples of suitable buffers are all salts of weak acids and strong bases or strong acids and weak bases, it being possible for the salts to be of the same acids or bases or mixtures of different acids or bases.

It is preferred in this connection for the buffering range of the buffer system to be chosen between pH 1 to 7. Suitable buffers or buffer solutions with a buffering range in acidic medium between pH 1 to 7 are, for example, buffers such as Walpole buffer (acetic acid/Na acetate, pH 3.6–5.6), Gomori aconitate buffer (aconitic acid/NaOH, pH 2.5–5.7), Kolthoff buffer (borax/succinate, pH 3.0–5.8), Sorensen citrate buffer (disodium citrate/HCl, pH 2.2–4.8), Sorensen glycine I buffer (glycine, NaCl/HCl, pH 1.2–3.6), Clark and Lub phthalate I buffer (potassium biphthalate/HCl, pH 2.2–3.8), Clark and Lub phthalate II buffer (potassium biphthalate/NaOH, pH 4.0–6.2), Smith and Smith piperazine buffer (pi-perazine, HCl/NaOH, pH 4.8–7.0), Clark and Lub potassium chloride/HCl buffer (KCl/HCl, pH 1.0–2.2), Gomori tris maleate buffer (tris maleate/NaOH, pH 5.2–8.6) or Gomori succinate buffer (succinate/NaOH, pH 3.8–6.0). Buffers such as MES, ADA, PIPES or ACES, which are buffers customary in biochemistry, or amino acid buffers are also suitable buffers.

Preferred buffers are those which can advantageously be prepared from weak acids and their salts, such as, for example, sodium acetate/acetic acid, sodium borate/boric acid, sodium phosphate/phosphoric acid, bicarbonate/sodium carbonate, sodium hydroxide/citric acid, sodium hydroxide/tartaric acid. Buffers of weak bases and their salts are also suitable. It is possible to use individual buffers or mixtures for adjusting the pH in the dispersions.

It is also possible to use buffer systems with a buffer range between pH 7 to 13. Suitable buffers and buffer solutions with a buffering range in basic medium between pH 7 to 13 are, for example, buffers such as Clark and Lub borate buffer (boric acid, KCl/NaOH, pH 7.8–10.0), Delory and King buffer (carbonate/bicarbonate, pH 9.2–10.7) or Sørensen glycine II buffer (glycine, NaCl/HCl, pH 8.4–13). Buffers such as cholamine chloride, BES, TES, HEPES, acetamidoglycine, glycinamide, tris, bicine, tricine or glycylglycine, which are buffers customary in biochemistry, or amino acid buffers are also suitable buffers Buffer systems which can also be used are salts, for example sodium salts of succinic acid, pyruvic acid, maleic acid, malonic acid, malic acid, lactic acid and other amino acids. It is also possible to consider as buffer salts of polyacrylic acid, polymethacrylic acid, acrylic acid/methacrylic acid copolymers, carboxymethylcellulose, carboxymethyl starch, hemiesters of cellulose, hydroxypropylmethylcellulose or polyvinyl alcohol with polybasic acids such as phthalic acid, succinic acid or trimellitic acid.

It is possible with this aqueous polymer dispersion, without the need for redispersion with the disadvantages associated therewith, to apply homogeneous film coatings with great reproducibility in a simple process step, in particular to pharmaceutical, agrochemical or nutritional dosage forms, which adhere extremely well, are resistant to external influences and ensure reproducible release of active ingredient. Compared with powders which are redispersible in $H_2O$, the amount which must be applied to achieve a particular release rate is less, thereby saving further costs.

"Nutritional dosage forms" mean tablets, capsules, granules or similar solid forms which do not contain active pharmaceutical ingredients but contain food supplements such as vitamins, carotenoids, minerals, plant extracts or nutraceuticals.

The preparations of the invention are unexpectedly insensitive to other auxiliaries normally employed in spray preparations, such as pigments, fillers, thickeners, suspension stabilizers, emulsifiers, gloss improvers, release accelerators etc. and to shear stress and variations in the coating process. Because the (polymer).films are very elastic, no fissuring occurs on storage because the coatings comply with the changes in shape of the core, for example caused by a change in ambient humidity. Coatings of this type are therefore also stable in regions with extremes of climate such as cold or high humidity.

It has surprisingly emerged that the aqueous polymer dispersions of the invention—although they were prepared with the aid of a regulator and thus tend to have low molecular weights and K values—are not at all tacky and can be sprayed distinctly more quickly onto solid dosage forms than the preparations previously disclosed, without agglomeration or sticking together of shaped articles or the coating becoming rough. This increased spraying rate is associated with a distinct cost vantage on use. The coating process is speeded up further through an increase in the inlet air temperature and the solids concentration in the spray solution. This is not possible with conventional preparations.

The dosage forms coated with the aqueous polymer dispersions of the invention show excellent reproducibility of properties such as, for example, the release, which is due inter alia to the good film-forming properties.

Release of active ingredient can be speeded up appropriately by additions of water-soluble substances, in particular of water-soluble polymers, so that it is also possible to form rapid-release coatings or coatings for taste masking.

Besides the coating of pharmaceutical dosage forms it is also possible to employ the aqueous polymer dispersions of the invention, but also the polymer powders produced therefrom in the conventional way, advantageously for coating detergent or dishwashing composition granules or tablets.

The coating of or incorporation into fragrance and flavoring preparations allows release thereof to be adjusted deliberately and, in this way, the effect to be prolonged.

Because of the good spray and film-forming properties, and the good skin compatibility, of the aqueous polymer dispersions of the invention or the polymer powders produced therefrom they are additionally suitable for producing wound dressing sprays which can be employed with active ingredients (e.g. in the form of disinfectant pump sprays) or without active ingredients in order to cover and treat wounds. It is a particular advantage in this connection that the film is homogeneous, scarcely impedes cutaneous respiration, adheres very well to the skin, is, owing to its flexibility, unimpaired even by large movements of the skin, but can be removed as a whole even after moistening with water, with no residues remaining on the skin or wound. This is not the case with the acrylic/methacrylic esters normally employed.

The aqueous polymer dispersions of the invention or the polymer powders produced therefrom are generally suitable not only for producing wound dressing sprays but also for all products which are to be sprayed onto the skin, parts of the body or articles. For example, such spray preparations which have been colored can be sprayed without difficulty onto window panes or automobile windows and then produce pictures or patterns depending on the template used, which can be removed again in a simple manner after moistening with water.

The aqueous polymer dispersions of the invention or the polymer powders produced therefrom have a large uptake capacity for active ingredients and can easily be processed to transdermal therapeutic systems which are highly compatible with the skin. In addition, it is possible and advantageous to produce so-called acne plasters which, applied overnight, heal blackheads, pimples and pustules.

The aqueous polymer dispersions of the invention or the polymer powders produced therefrom are also suitable for producing cosmetic preparations, in particular sunscreen preparations.

The aqueous polymer dispersions of the invention are distinguished in that the polyvinyl acetate present therein preferably has a K value of from 45 to 95, in particular 65 to 85. The K value desired in each case can be adjusted to a certain extent in a manner known per se through the choice of the polymerization conditions, for example the polymerization time and the initiator concentration. The K value of the polymers of the invention is adjusted by the use of a regulator. The K values are measured as described by Fikentscher, Cellulosechemie, vol. 13, pp. 58–64 and 71–74 (1932) at 25° C. in 0.1% by weight aqueous solution, but in practice also in other, even nonaqueous solutions with different polymer concentrations. The measurement in this case preferably takes place in a tetrahydrofuran solution containing 1% by weight of polymer.

The protective colloid present in the aqueous dispersion of the invention is preferably polyvinylpyrrolidone, in an amount between 5 and 20% by weight based on vinyl acetate monomer, which particularly preferably has a K value of from 20 to 40. It is also possible in addition to employ other water-soluble or water-swellable protective colloids such as, for example, cellulose derivatives, preferably hydroxypropylmethylcellulose, methylcellulose or hydroxyethylcellulose, galactomanan, pectin, xanthan, polyvinyl alcohol, acrylate/methacrylate copolymers, sodium carboxymethyl starch, cellulose, degraded starches, maltodextrins etc. The auxiliaries can moreover be added before, during and after the polymerization.

The dispersion has a solids content of from 10 to 45% by weight, preferably of from 15 to 35% by weight.

The aqueous polymer dispersion of the invention has the additional feature that the viscosity of the dispersion with the abovementioned solids content is in the range from 5 to 500 mPas, preferably in the range from 10 to 250 mPas, particularly preferably in the range from 15 to 100 mPas.

The ionic emulsifier present in the aqueous dispersion of the invention can be a conventional ionic emulsifier such as, for example, alkali metal and ammonium salts of alkyl sulfates (alkyl radical: $C_8$ to $C_{16}$), of alkylsulfonic acids (alkyl radical: $C_8$ to $C_{16}$), of sulfuric acid monoesters of ethoxylated alkanols (EO degree: 4 to 100, alkyl radical: $C_{12}$ to $C_{16}$), and ethoxylated alkylphenols (EO degree 3 to 50, alkyl radical: $C_4$ to $C_{12}$), and of alkylarylsulfonic acids (alkyl radical: $C_9$ to $C_{18}$). Other anionic emulsifiers which have proved advantageous are compounds such as Dowfax 2A1 (brand name of Dow Chemical Company). Sodium lauryl sulfate is preferred. The ionic emulsifier is employed in concentrations of from 0.2 to 5% by weight based on the total weight of the monomer content.

It is also possible in addition to employ conventional nonionic emulsifiers.

The free-radical initiator employed for the polymerization is preferably Na-, K- or ammonium-peroxodisulfate, but other free-radical initiators which are customary per se, such as hydrogen peroxide, organic peroxides, hydroperoxides or azo compounds, are also possible - also in conjunction with redox components such as, for example, ascorbic acid.

The ratio of free-radical initiator to buffer system is preferably between 1:3 and 3:1 by weight.

The aqueous polymer dispersion of the invention is a so-called "regulated" polymer dispersion, i.e. the dispersion is carried out in the presence of a polymerization regulator, particularly suitable regulators being sulfur-containing compounds such as, for example, thioglycol, t-dodecyl mercaptan, n-dodecyl mercaptan and ethylhexyl thioglycolate, which result inter alia in being able to adjust the K values preferred according to the invention and in the resulting polymers having sulfur-containing end groups. The total amount of the regulator, normally between 0.05 and 1%, preferably between 0.1 and 0.5%, in each case based on the total monomer content, is preferably introduced in the emulsion feed.

Besides the molecular weight or K value, particularly important for producing coatings is the size of the dispersion particles. The polymer dispersion of the invention therefore preferably has dispersion particles having an average size of only 50 to 300 nm, preferably from 100 to 200 nm. The determination takes place in a conventional way, for example by means of an ultracentrifuge, photon correlation spectroscopy or by determining the transmittance of light. The particle size is normally controlled via the emulsifier concentration. The dispersion particles obtained according to the invention are very fine although a considerable amount of a nonionic protective colloid is present in the initial charge for the polymerization. By contrast, U.S. Pat. No. 5,252,704 discloses that such ratios preferentially result in coarse-particle dispersions.

The present invention also relates to a process for preparing an aqueous polymer dispersion, in which vinyl acetate is polymerized by free-radical polymerization in the presence of at least one ionic emulsifier, at least one free-radical initiator and at least one protective colloid, wherein the polymerization is carried out in the presence of a polymerization regulator and wherein the ratio by weight of protective colloid to ionic emulsifier is at least 4:1, preferably at least 8:1, particularly preferably in the range between 8:1 and 12:1, and wherein the ratio by weight of vinyl acetate monomer to protective colloid is between 19:1 and 4:1, preferably between 15:1 and 6:1. The ratio by weight of free-radical initiator to buffer system is preferably between 1:3 and 3:1.

The polymerization preferably takes place at a pH in the range from 1 to 7, particularly preferably in the range from 3 to 6. It is possible, depending on the settings of the polymerization reactors, for the pH to be adjusted to the desired pH during the reaction by suitable measuring and control devices.

For the preferred embodiment of the process of the invention, the pH is kept constant during the polymerization by addition of one of the reagents with a basic action which has already been described at the outset or are particularly preferably, by the buffer systems already mentioned.

However, it is also possible to polymerize vinyl acetate without additional pH control. In this case, after the polymerization, the pH of the aqueous dispersion is ordinarily adjusted by addition of one of the buffer systems mentioned at the outset to a value in the range from 1 to 7, preferably 3 to 6. It is possible by this subsequent pH control to improve the storage stability of the aqueous polymer dispersion.

The emulsion polymerization is carried out in a manner known per se at temperatures of from 40° C. to 95° C. under an atmospheric pressure or, preferably at temperatures of from 55° C. to 80° C. under a pressure of from 1.1 to 15 bar, particularly preferably under a pressure of from 1.5 to 6 bar. The desired pressure can be adjusted in this case by feeding nitrogen into the reactor before and/or during the polymerization, preferably before the polymerization.

This process is preferably carried out as a semicontinuous feed process with the total amount of the protective colloid being present in the initial charge. Another preferred procedure comprises more than 50 of 100 parts of the ionic emulsifier being present in the initial charge.

The present invention further relates to the use of the aqueous polymer dispersions of the invention as auxiliary for pharmaceutical, agrochemical or nutritional dosage forms, in particular as coating agent for solid pharmaceutical, agrochemical or nutritional dosage forms. It additionally relates to the use of the dispersion of the invention or of the powders produced therefrom as auxiliary, in particular coating agent, in detergent, dishwashing and cleaning compositions of any type, especially when they are in the form of granules.

The invention further relates to the use of the dispersion of the invention or of the powders produced therefrom as coating or embedding agents for fragrances and flavorings.

The invention further relates to the use of the dispersions of the invention and of the powders produced therefrom for producing preparations which are sprayed onto surfaces, in particular the human or animal skin, especially for wound dressing sprays or for producing transdermal therapeutic systems or else for producing cosmetic preparations, especially sunscreen preparations.

PREPARATION EXAMPLE 343.7 g of water, 1.8 g of Na lauryl sulfate (100% pure), 74.7 g of polyvinylpyrrolidone with a K value of 30 (30% strength in $H_2O$) and 63.5 g of a portion of feed 1 (see below) were introduced into a 2 l reaction vessel with anchor stirrer and heated to 75° C.

At 65° C., feed 2 (see below) was added within 10 minutes and, at 75° C., feed 1 was metered in over the course of 2 h and feed 3 (see below) was metered in over the course of 3 h.

After completion of the feeds, polymerization was continued at 75° C. for 2 h. After cooling, the pH was adjusted to about 5 with 1% strength NaOH.

A 30% strength dispersion (solids content 30%) with a K value of 71 (measured as 1% strength solution in tetrahydrofuran) and a particle size of 121 nm was obtained. The coagulum content of the dispersion was very small (0.2 g of coagulum on the stirrer and in the 0.120 μm filter). The pH remained unchanged over 3 months.

| Feed 1: | 298.8 g of VAc |
| --- | --- |
|  | 1.2 g of Na lauryl sulfate 100% pure |
|  | 333.0 g of water |
|  | 0.9 g of ethylhexyl thioglycolate |
|  | 0.75 g of sodium acetate*3$H_2O$ |
| Feed 2: | 0.45 g of Na peroxodisulfate |
|  | 6.0 g of water |
| Feed 3: | 0.9 g of Na peroxodisulfate |
|  | 12.1 g of water |

EXAMPLE 1

Sustained Release Propranolol Pellets

Propranolol HCl pellets with a particle size of 0.5 to 1.5 mm and an active ingredient content of 20% were coated in a fluidized bed with the polyvinyl acetate dispersion of the invention (from the Preparation Example).

The coating dispersion had the following composition:

| polyvinyl acetate dispersion 30% | 50.0% |
| --- | --- |
| propylene glycol | 1.7% |
| talc | 5.0% |
| water | 43.3% |

The solids content of the spray suspension was 23.4%.

The spray dispersion was prepared by respectively dissolving and suspending propylene glycol and talc in water and then homogenizing with a corundum disk mill. This suspension was slowly introduced into the 30% strength polyvinyl acetate dispersion while stirring. 500.0 g of this spray preparation were sprayed onto 500 g of propranolol pellets in a fluidized bed in an Aeromatic Strea 1 (from Aeromatic).

Spraying Conditions:

| Nozzle: | 0.8 mm |
| --- | --- |
| Inlet air temperature: | 60° C. |
| Outlet air temperature: | 35° C. |
| Spraying pressure: | 0.8 bar |
| Spraying rate: | 15 g/min |
| Drying: | 50° C./5 mm |

The pellet coating was very smooth and uniform. No twins were formed.

The release was determined by packing the coated pellets, in an amount equivalent to 160 mg of propranolol HCl into gelatin capsules and releasing them over 2 h in simulated gastric fluid (0.08-N HCl) in a paddle release apparatus (from Pharmatest) at 37° C. and 50 revolutions/min. After 2 h, the buffer was changed to pH 6.8 by adding a phosphate buffer concentrate. The following values were determined for release:

| 1 h | 2% |
| --- | --- |
| 2 h | 5% |
| 4 h | 10% |
| 8 h | 35% |
| 12 h | 55% |
| 16 h | 74% |
| 20 h | 91% |
| 24 h | 99% |

The release from the uncoated pellets was very rapid at 98% after 45 min.

EXAMPLE 2

Sustained Release Diclofenac Pellets

Diclofenac sodium pellets with a particle size of 0.7 to 1.5 mm and an active ingredient content of 30% were coated in a fluidized bed with the polyvinyl acetate dispersion of the invention.

The coating dispersion had the following composition:

| Polyvinyl acetate dispersion 30% | 58.0% |
| --- | --- |
| Propylene glycol | 2.6% |
| Water | 39.4% |

The solids content of the spray suspension was 20%.

The spray dispersion was prepared by dissolving propylene glycol in water and slowly introducing into the 30% strength polyvinyl acetate dispersion while stirring. 964.0 g of this spray preparation were sprayed onto 500 g of diclofenac sodium pellets in a fluidized bed in an Aeromatic Strea 1 (from Aeromatic).

Spraying Conditions:

| | |
|---|---|
| Nozzle: | 0.8 mm |
| Inlet air temperature: | 55 ° C. |
| Outlet air temperature: | 34 ° C. |
| Spraying pressure: | 1.2 bar |
| Spraying rate: | 18 g/min |
| Drying: | 45° C./5 min |

The pellet coating was very smooth and uniform. No twins were formed.

The release was determined by packing the coated pellets, in an amount equivalent to 100 mg of diclofenac sodium, into gelatin capsules and releasing them over 2 h in simulated intestinal fluid (phosphate buffer pH 6.8) in a paddle release apparatus (from Pharmatest) at 37° C. and 50 revolutions/min.

The values determined for the release were as follows:

| | |
|---|---|
| 1 h | 6% |
| 2 h | 16% |
| 4 h | 41% |
| 8 h | 89% |
| 12 h | 100% |

The values for the release from uncoated pellets were 99% after 1 h.

EXAMPLE 3

Slow-Release Ascorbic Acid

Ascorbic acid crystals with a particle size of 0.5 to 1.5 mm were coated in a fluidized bed in a Huttlin Kugelcoater (from Huttlin) with the polyvinyl acetate dispersion of the invention.

The coating dispersion had the following composition:

| | |
|---|---|
| Polyvinyl acetate dispersion 30% | 50.0% |
| Propylene glycol | 1.7% |
| Talc | 7.0% |
| Sicovit Rot 30 (red iron oxide) | 1.0% |
| Water | 40.3% |

The solids content of the spray suspension was 26.4%.

The spray dispersion was prepared by respectively dissolving and suspending propylene glycol and talc and Sicovit Rot 30 in water and then homogenizing with a corundum disk mill. This suspension was slowly introduced into a 30% strength polyvinyl acetate dispersion with stirring. 4500.0 g of this spray preparation were sprayed onto 3000 g of ascorbic acid crystals in a fluidized bed in a Huttlin HKC 5 Kugelcoater (from Huttlin).

Spraying Conditions:

| | |
|---|---|
| Nozzle: | 0.8 mm |
| Inlet air temperature: | 60° C. |
| Outlet air temperature: | 35° C. |
| Spraying pressure: | 1.2 bar |
| Spraying rate: | 69 g/min |
| Drying: | 50° C./5 min |

The coating was very smooth and uniform. No twins were formed.

The release was determined by packing the coated crystals, in an amount equivalent to 500 mg of ascorbic acid, into gelatin capsules and releasing these in simulated gastric fluid (0.1-N HCl) in a paddle release apparatus (from Pharmatest) at 37° C. and 50 revolutions/min.

The values determined for the release were as follows:

| | |
|---|---|
| 1 h | 4% |
| 2 h | 9% |
| 4 h | 28% |
| 8 h | 49% |
| 12 h | 69% |
| 16 h | 85% |

20 h 98%

By contrast, the release from the uncoated crystals was very rapid (100% after 1 h).

EXAMPLE 4

Wound Dressing Spray

A propellant gas aerosol which forms a film on the skin or on wounds is produced by stirring 133.3 g of 30% strength polyvinyl acetate dispersion of the invention into 366.7 g of ethanol. A 6 oz aerosol can is charged with 50.0 g of this mixture and closed with a suitable valve. Then 50.0 g of dimethyl ether are forced into the aerosol can under pressure.

After spraying onto the skin, a homogeneous film forms and adheres very strongly and is very elastic.

EXAMPLE 5

Film-Forming Disinfectant Pump Spray With Cetylpyridinium Chloride 400.0 g of the 30% strength polyvinyl acetate dispersion are mixed with 50.0 g of a 30% strength solution of polyvinylpyrrolidone K 30 in water and freeze dried. 30.0 g of this powder are dissolved in 570.0 g of an ethanol/water mixture (19:1) and, while stirring, 1.0 g of cetylpyridinium chloride and then 399.0 g of ethyl acetate are added. 100 ml pump spray bottles with a suitable spray head delivering 0.1 ml are charged with this preparation.

After spraying onto the skin, a flexible film forms and adheres very well.

EXAMPLE 6

Acne Plaster 32.0 g of a 25% strength aqueous solution of polyvinylpyrrolidone with a K value of 90 are added to 120.0 g of 30% strength polyvinyl acetate dispersion while stirring.

Then 0.04 g of thimerosal and 0.5 g of dexpanthenol are dissolved in 2.0 g of water and 8.0 g of propylene glycol and slowly added to a mixture of polyvinyl acetate dispersion and polyvinylpyrrolidone while stirring. This preparation is applied by means of an Erichsen film-drawing apparatus using a 200 μm knife onto a 40 μm thick polyester sheet (Hostaphan, from Hoechst). After drying at 55° C., the knife-application process is repeated twice in order to result in a layer thickness of about 200 μm. The dried film is covered with a siliconized release liner. The individual plasters with an area of 1 cm$^2$ are produced by punching.

EXAMPLE 7

Transdermal Therapeutic System With Propranolol 40.0 g of N-pyrrolidone, 20.0 g of propranolol HCl and 20.0 g of polyvinylpyrrolidone with a K value of 90 are dissolved in 40.0 g of demineralized water. This solution is incorporated into 333.3 g of 30% strength polyvinyl acetate dispersion of the invention while stirring. A 200 μm knife is used to spread this mixture onto a 40 μm-thick polyester sheet, which is then dried at 60° C. The spreading process is repeated once more to increase the layer thickness. After covering the polymer layer with a siliconized released liner it is possible to punch out any desired shapes.

EXAMPLE 8

Sunscreen Preparation 25.0 g of Uvinul MC 80 (2-ethylhexyl p-methoxycinnamate), 20.0 g of tocopheryl acetate, 25.0 g of isopropyl myristate and 15.0 g of Cremophor RH 40 are dissolved in 150.0 g of ethanol at 40° C. while stirring. Then 50.0 g of demineralized water, 150.0 g of propylene glycol, 50.0 g of glycerol and 25.0 g of dried polyvinyl acetate dispersion are incorporated while stirring. The preparation is cooled to room temperature and used to fill lotion bottles or spray bottles.

We claim:

1. An aqueous dispersion of homopolymer polyvinyl acetate prepared by free-radical polymerization of vinyl acetate monomer in the presence of at least one ionic emulsifier, at least one free-radical initiator and at least one protective colloid, wherein the polymerization is carried out in the presence of a polymerization regulator and wherein the ratio by weight of protective colloid to ionic emulsifier is at least 4:1 and wherein the ratio by weight of the vinyl acetate monomer to protective colloid is between 19:1 and 4:1.

2. The aqueous dispersion as claimed in claim 1, wherein the polymerization is carried out at a pH in the range from 1 to 7.

3. The aqueous dispersion as claimed in claim 1, wherein the pH during the polymerization is kept constant by addition of a reagent with a basic action.

4. The aqueous dispersion as claimed in claim 3, wherein an alkali metal hydroxide or alkaline earth metal hydroxide is used as reagent with a basic reaction.

5. The aqueous dispersion as claimed in claim 1, wherein the pH is kept constant during the polymerization by addition of a buffer system.

6. The aqueous dispersion as claimed in claim 5, wherein salts of weak acids and strong bases or salts of strong acids and weak bases or mixtures thereof are used as buffer system.

7. The aqueous dispersion as claimed in claim 6, wherein the buffer system is a salt of an acid selected from the group consisting of carbonic acid, boric acid, acetic acid, citric acid, tartaric acid and phosphoric acid.

8. The aqueous dispersion as claimed in claim 5, wherein the ratio by weight of free-radical initiator to buffer system is between 1:3 and 3:1.

9. The aqueous dispersion as claimed in claim 1, wherein the polymerization is carried out in the presence of a free-radical initiator selected from the group consisting of sodium, potassium or ammonium peroxodisulfate.

10. The aqueous dispersion as claimed in claim 1, wherein the K value of the polyvinyl acetate is from 45 to 95.

11. The aqueous dispersion as claimed in claim 1, wherein the protective colloid is polyvinylpyrrolidone.

12. The aqueous dispersion as claimed in claim 11, wherein the protective colloid is polyvinylpyrrolidone with a K value of from 20 to 40.

13. The aqueous dispersion as claimed in claim 1, wherein the ionic emulsifier is sodium lauryl sulfate.

14. The aqueous dispersion as claimed in claim 1, wherein the polymerization regulator is a sulfur-containing compound.

15. The aqueous dispersion as claimed in claim 1, wherein the average particle size of the dispersion particles is in the region of 50 to 300 nm.

16. The aqueous dispersion as claimed in claim 1, which has a solids content of from 10 to 45% by weight.

17. The aqueous dispersion as claimed in claim 16, wherein the viscosity of the dispersion is in the range from 5 to 500 mPas.

18. A process for preparing an aqueous dispersion of homopolymer polyvinylacetate in which vinyl acetate monomer is polymerized by free-radical polymerization in the presence of at least one ionic emulsifier, at least one free-radical initiator and at least one protective colloid, wherein the polymerization is carried out in the presence of a polymerization regulator and wherein the ratio by weight of protective colloid to ionic emulsifier is at least 4:1 and wherein the ratio by weight of vinyl acetate monomer to protective colloid is between 19:1 and 4:1.

19. The process as claimed in claim 18, wherein the polymerization is carried out at a pH in the range from 1 to 7.

20. The process as claimed in claim 18, wherein the pH during the polymerization is kept constant by addition of a reagent with a basic action.

21. The process as claimed in claim 20, wherein an alkali metal or alkaline earth metal hydroxide is used as reagent with a basic reaction.

22. The process as claimed in claim 18, wherein the pH is kept constant during the polymerization by addition of a buffer system.

23. The process as claimed in claim 22, wherein the ratio by weight between free-radical initiator and buffer system is between 1:3 and 3:1.

24. The process as claimed in claim 18, wherein the aqueous dispersion is prepared in a semicontinuous feed process with the total amount of the protective colloid being present in the initial charge.

25. The process as claimed in claim 18, wherein more than 50 of 100 parts of the ionic emulsifier are present in the initial charge.

26. The process as claimed in claim 18, wherein the polymerization is carried out at a temperature below 800° C.

* * * * *